(12) United States Patent
Dainobu et al.

(10) Patent No.: US 9,468,734 B2
(45) Date of Patent: Oct. 18, 2016

(54) GAS FLOW SYSTEM, ADAPTOR, AND METHOD

(75) Inventors: Hidetoshi Dainobu, Tokyo (JP);
Masayuki Inoue, Tokyo (JP);
Fumihiko Takatori, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 339 days.

(21) Appl. No.: 12/697,741

(22) Filed: Feb. 1, 2010

(65) Prior Publication Data

US 2011/0028858 A1    Feb. 3, 2011

(30) Foreign Application Priority Data

Feb. 17, 2009  (JP) ................. 2009-033627

(51) Int. Cl.
| | |
|---|---|
| A61B 5/08 | (2006.01) |
| A61M 16/08 | (2006.01) |
| A61B 5/097 | (2006.01) |
| A61B 5/083 | (2006.01) |
| A61B 5/087 | (2006.01) |
| A61M 16/10 | (2006.01) |

(52) U.S. Cl.
CPC .......... *A61M 16/0816* (2013.01); *A61B 5/097* (2013.01); *A61B 5/083* (2013.01); *A61B 5/087* (2013.01); *A61M 2016/102* (2013.01); *A61M 2205/3306* (2013.01); *A61M 2230/43* (2013.01)

(58) Field of Classification Search
USPC ............ 128/204.22, 204.23, 205.12, 205.23; 600/532
See application file for complete search history.

(56) References Cited

U.S. PATENT DOCUMENTS

| | | | | |
|---|---|---|---|---|
| 3,683,693 | A | * | 8/1972 | Brown ....................... 73/861.65 |
| 5,038,773 | A | * | 8/1991 | Norlien et al. .......... 128/205.23 |
| 5,445,160 | A | * | 8/1995 | Culver et al. ................. 600/532 |
| 5,535,633 | A | * | 7/1996 | Kofoed et al. ............. 73/861.52 |
| 5,957,127 | A | | 9/1999 | Yamamori et al. |
| 6,142,148 | A | * | 11/2000 | Weckstrom et al. ..... 128/204.22 |
| 6,216,692 | B1 | | 4/2001 | Todokoro et al. |
| 6,512,581 | B1 | * | 1/2003 | Yamamori et al. ........... 356/246 |
| 6,742,399 | B2 | * | 6/2004 | Kunz et al. ................. 73/861.52 |
| 6,802,225 | B2 | * | 10/2004 | Shahar et al. ............. 73/861.52 |
| 7,335,164 | B2 | * | 2/2008 | Mace et al. .................... 600/532 |
| 2002/0029003 | A1 | * | 3/2002 | Mace et al. .................... 600/532 |
| 2008/0283062 | A1 | * | 11/2008 | Esposito, Jr. ............ 128/204.23 |
| 2009/0250059 | A1 | * | 10/2009 | Allum et al. ............. 128/204.26 |

FOREIGN PATENT DOCUMENTS

| | | |
|---|---|---|
| JP | 2001-66243 A | 3/2001 |
| JP | 2009-028551 A | 2/2009 |

* cited by examiner

*Primary Examiner* — Navin Natnithithadha
*Assistant Examiner* — Michael R Bloch
(74) *Attorney, Agent, or Firm* — Kenealy Vaidya LLP

(57) ABSTRACT

An airway adaptor that measures the concentration of at least one of a specific component and the flow rate of a supply gas and a return gas. The airway adapter may include a tube having a flow path in which the supply gas and the return gas passes. The tube may include a first end having a first aperture for guiding the supply gas into the flow path, and second end having a second aperture for guiding the return gas. Further, the airway adapter may include a measurement device operable to measure at least one of the supply gas and the return gas in the air flow path and a partial shielding disposed at the first aperture and structured to shield a portion of the air flow path. The supply gas may be a respiratory gas and the return gas may be inhaled or exhaled breath of a person.

20 Claims, 7 Drawing Sheets

GAS FLOW SYSTEM, ADAPTOR, AND METHOD

BACKGROUND

This application claims priority to Japanese Patent Application No. 2009-033627 filed on Feb. 17, 2009 in the Japan Patent Office, the disclosure of which is incorporated herein in its entirety by reference.

1. Field

The presently disclosed subject matter relates to a gas flow system, adaptor, and method, and more particularly to a gas flow system, adaptor, and method that may include a respiratory concentration sensor that measures the concentration of a selected component in the respiratory system, such as a gas including exhaled or inhaled air of a person who will be measured, a respiratory flow sensor that measures the respiratory flow rate, and an airway adaptor for use in these sensors.

2. Description of the Related Art

In the related art, a respiratory gas sensor for optically measuring the concentration of, for example, carbon dioxide in a person's breath is shown in Japanese published unexamined application No. 2001-66243. Such a sensor can optically detect the change over time of the concentration of, for example, carbon dioxide in the respiratory by passing the breath such as exhaled or inhaled air of a person who is being measured through an airway adaptor equipped with an optical sensor. In addition, there is also a method of measuring the concentration by sampling a portion of the breath from the person whose respiration is being measured. When such a respiratory gas sensor is used in a patient who needs respiratory management assistance, the airway adaptor is usually provided between the tube inserted into a patient's body, for example, the trachea, and an artificial respirator. The respiratory flow rate sensor is also provided at the same location.

In the case of respiratory management in a patient using an artificial respirator in this way, air may be steadily supplied from the artificial respirator to the patient in addition to periodic insufflation. As such, it is difficult to accurately measure the breathing of a patient, such as an infant who has low ventilation, by a steady influx of air from the artificial respirator into an airway adaptor.

SUMMARY

In order to solve the problem mentioned above, exemplary embodiments of the presently disclosed subject matter may provide an airway adaptor operable to measure the concentration of at least one of a specific component and the flow rate of a supply gas 88 and a return gas 89. The airway adapter may comprise a tube having a flow path in which the supply gas and the return gas passes, the tube including a first end having a first aperture for guiding the supply gas into the flow path, and second end having a second aperture for guiding the return gas; a measurement device operable to measure at least one of the supply gas and the return gas in the air flow path; and a partial shielding disposed at the first aperture and structured to shield a portion of the air flow path. The supply gas may be a respiratory gas and the return gas may be inhaled or exhaled breath of a person.

The airway adaptor may also include a partial shielding part provided at the first aperture side for shielding a portion of said air flow path. The airway adaptor of the presently disclosed subject matter, in an exemplary embodiment, may have a pair of translucent windows that are provided facing opposite each other along the inner wall of said air flow path, allowing the detection light irradiated from the outside of the tube from a measurement device.

In this way, the gas, such as air can be suppressed from flowing into the air flow path of an airway adaptor even when the airway adaptor is connected to an artificial respirator that supplies air constantly.

Furthermore, in the airway adaptor of the presently disclosed subject matter, the pair of translucent windows may be provided along the inner wall mentioned above located by the side of the air flow path at the time of using the airway adaptor, with the partial shielding part shielding a portion excluding the lower side of said air flow path.

In this way, dew condensation water generated inside the air flow path, or that has flown inside the air flow path, is not stopped at the partial shielding part, preventing it from accumulating inside the flow path.

Moreover, in the airway adaptor of the presently disclosed subject matter, the partial shielding part may be provided in the proximity of said first aperture.

In this way, the inflow of the air into the air flow path can be effectively controlled.

Also, in the airway adapter of the presently disclosed subject matter, the partial shielding part may be provided integrally with the tube.

In this way, the partial shielding part can be provided in the tube without increasing the number of components.

Also, in the airway adapter of the presently disclosed subject matter, the width of the second aperture of the partial shielding part may be narrower than that of the first aperture.

In this way, the increase in the outflow resistance by said partial shielding part can be suppressed when the breath [exhaled air] from the person to be measured is emitted from the airway adaptor.

The presently disclosed subject matter may also include a respiratory concentration sensor that is equipped with an airway adaptor having either configuration mentioned above, as well as a part for optically measuring the concentration of a specific component in the breath of the person to be measured. Furthermore, in another exemplary embodiment, the respiratory flow rate sensor may be equipped with an airway adaptor having either configuration mentioned above, as well as a part for measuring the respiratory flow rate of the person to be measured.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

DETAILED DESCRIPTION OF EXEMPLARY EMBODIMENTS

Figure 1:
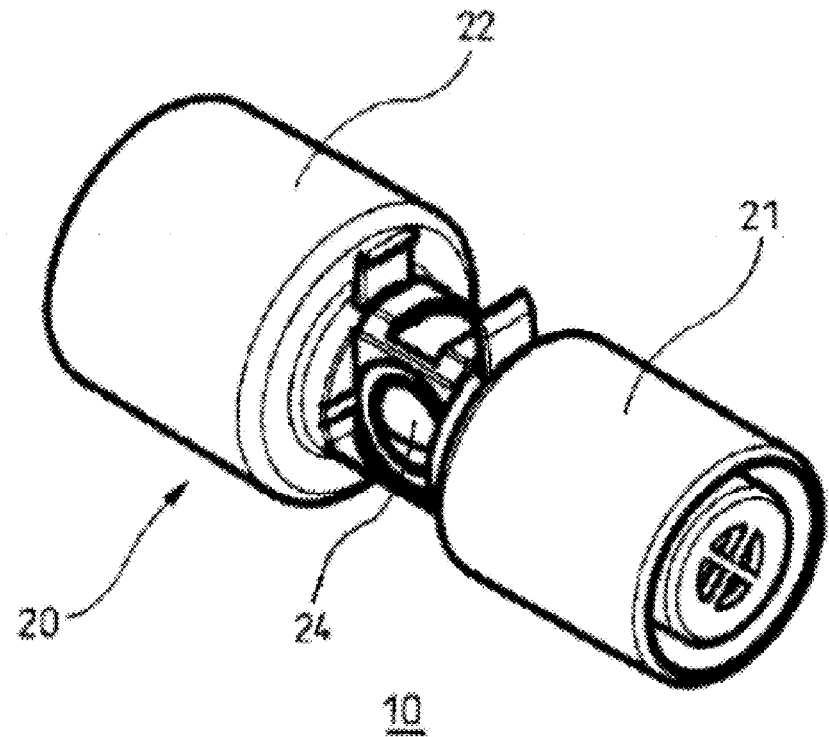
FIG. 1 is an external view of an exemplary embodiment of an airway adaptor.
Figure 2:
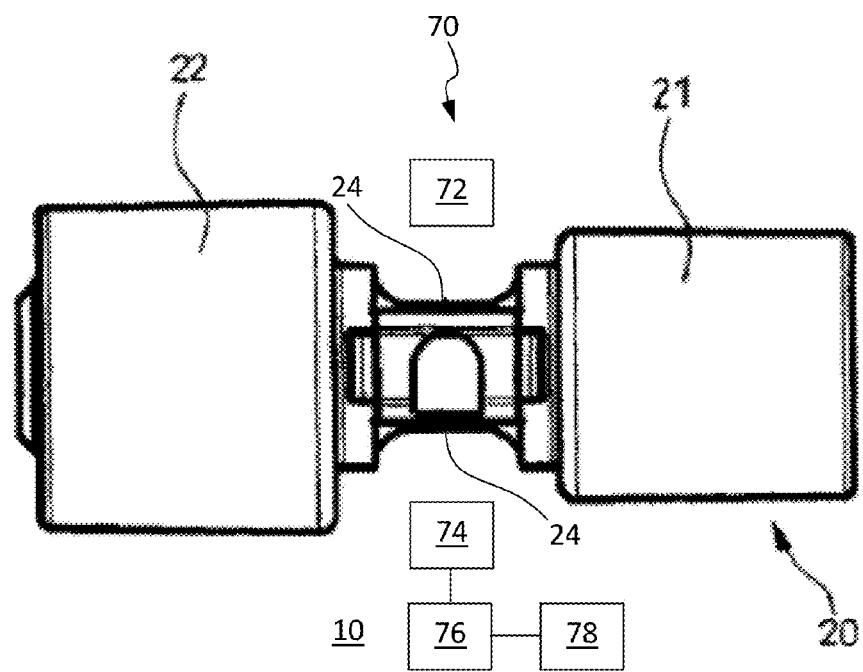
FIG. 2 is a top view of the airway adaptor.
Figure 3:
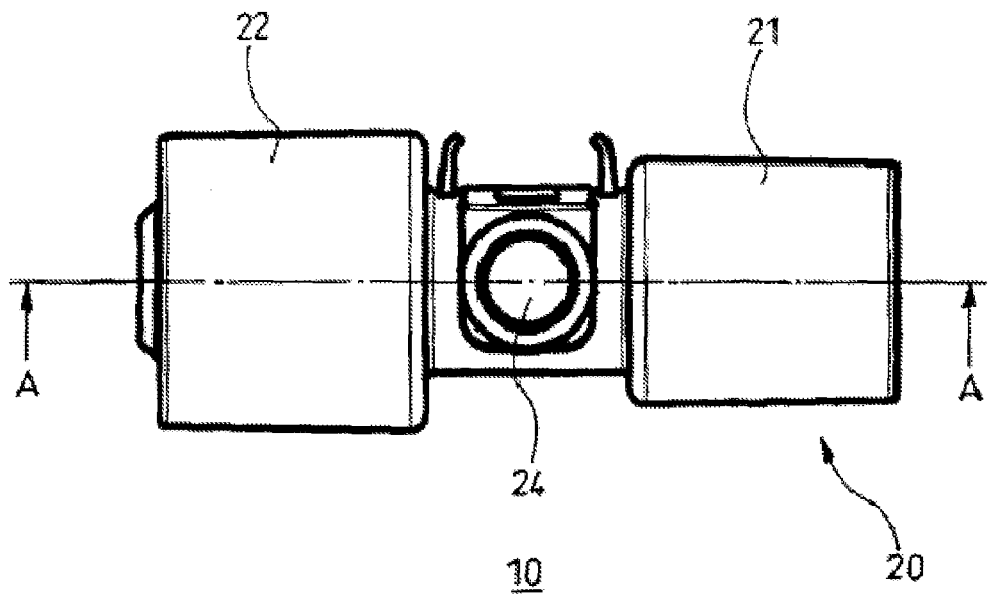
FIG. 3 is a front view of the airway adaptor.
Figure 4:
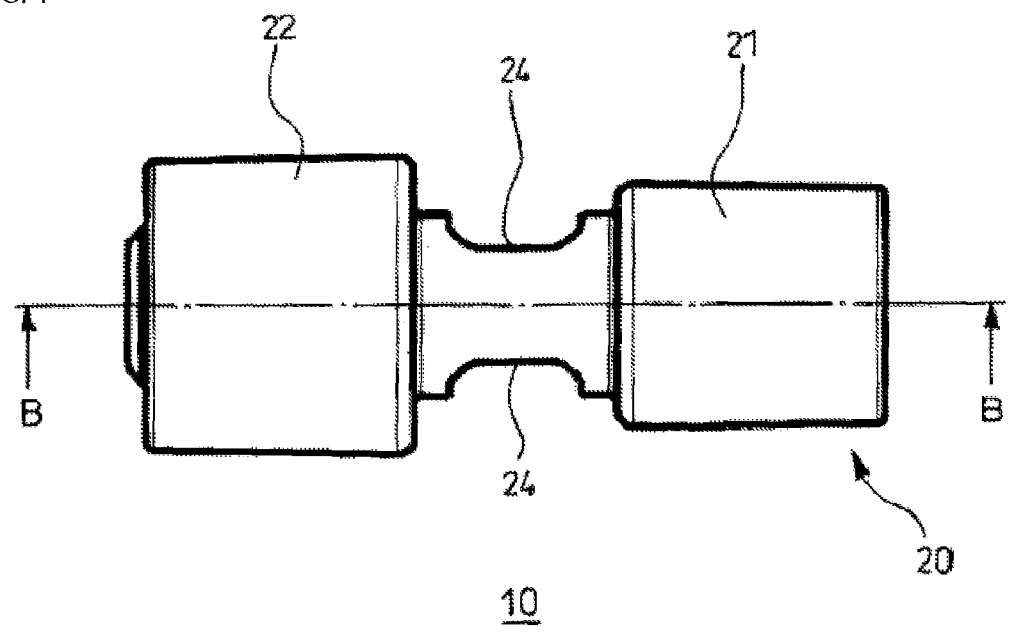
FIG. 4 is a bottom view of the airway adaptor.
Figure 5:
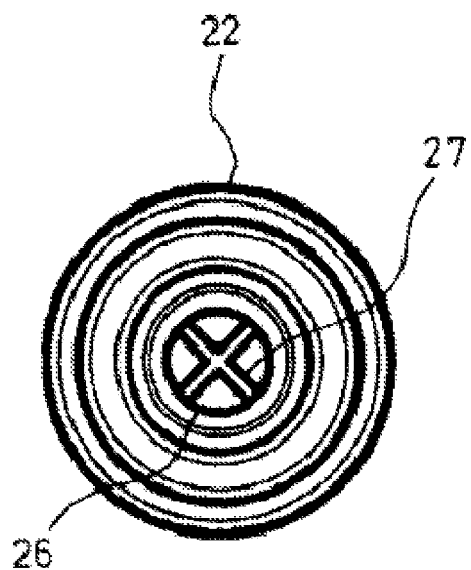
FIG. 5 is a left side view of the airway adaptor.
Figure 6:
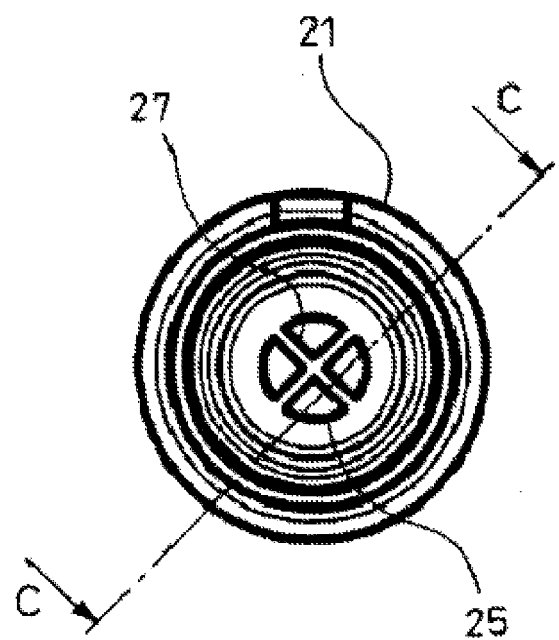
FIG. 6 is a right side view of the airway adaptor.
Figure 7:
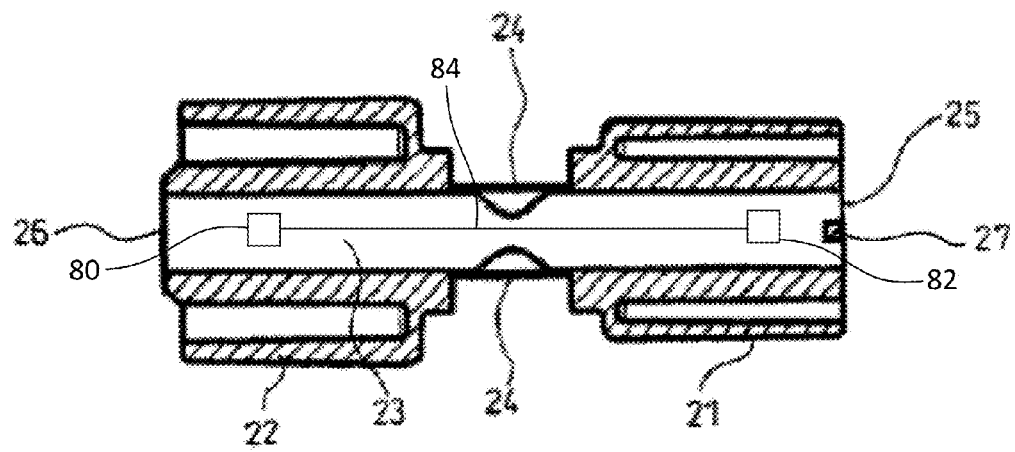
FIG. 7 is a cross-section of section A-A of FIG. 3.
Figure 8:
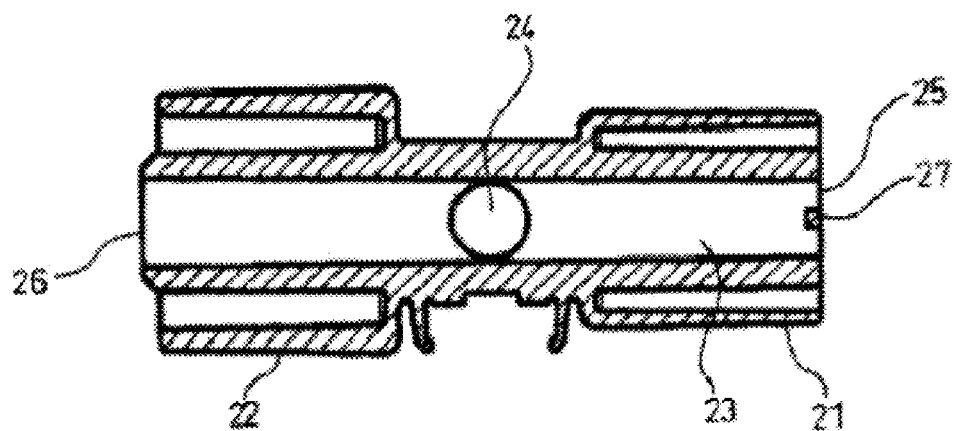
FIG. 8 is a cross-section of section B-B of FIG. 4.

The presently disclosed subject matter will now be described more fully with reference to the accompanying drawings. FIG. 1 is an external view of the airway adaptor 10 according to an exemplary embodiment of the presently disclosed subject matter. FIG. 2, FIG. 3, and FIG. 4 are top, front, and bottom views of the airway adaptor 10, respectively. FIG. 5 and FIG. 6 are left and right side views of the airway adaptor 10. FIG. 7 is a cross-section of section A-A of FIG. 3, and FIG. 8 is a cross-section of section B-B of FIG. 4.

Airway adaptor 10 may be used when optically measuring the concentration of a specific component in the breath of a person to be measured, for example, a patient who needs respiratory management, and it may be equipped with a tube 20 in which an air flow path 23 has been formed for passing through the respirator into the inside. This airway adaptor 10 may be used for measurement by connecting one end of the tube 20 to an air supply and respiratory outlet of an artificial respirator through a connecting part consisting of, for example, Y-shaped tube, etc., and connecting the other end of said tube 20 to a tube inserted into the trachea of a person to be measured, for example.

A respiratory-side adaptor 21 secured to said connecting part may be provided to one end of the tube 20, and a patient-side adaptor 22 secured to said tube may be provided to the other end. Moreover, a first aperture 25 may be provided to one end mentioned above in an air flow path 23 for guiding the air supplied from the artificial respirator during said measurement; a second aperture 26 may be provided to the other end mentioned above for guiding the exhaled air of a person being measured during said measurement.

At the air flow path 23, a pair of translucent windows 24 formed by a transparent part may be provided opposite each other along the inner wall of said air flow path 23. A measuring part 70 including a light-emitting part 72 and a light-receiving part 74 may be installed at the pair of translucent windows 24 during said measurement. More specifically, a light-emitting surface of the light-emitting part 72 that emits optical bandwidth (detected light) including absorption spectra of a component subjected to measurement in the breath, along with a light-receiving surface of the light-receiving part 74 that receives the detected light from said light-emitting part 72, may be installed at the pair of translucent windows 24 so that they are facing opposite to each other on the same optical axis.

By aligning the light-emitting part 72 and light-receiving part 74 in such a way as mentioned above with respect to the pair of translucent windows 24, the detected light emitted by the light-emitting part 72 may be transmitted through the pair of translucent windows 24, then received at the light-receiving part 74. In this way, the concentration of the component subjected to measurement included in the breath of a person to be measured can be measured by a processor 76 with a memory 78. As the component subjected to measurement, for example, carbon dioxide can be mentioned.

By the way, the airway adaptor 10 of this embodiment may be equipped with a partial shielding part 27 formed integrally with a tube 20 in the proximity of the first aperture 25 on the air flow path 23. The partial shielding part 27 may be provided so that it shields a portion of the air flow path 23, as shown in FIG. 1, FIG. 6, FIG. 7, and FIG. 8. This partial shielding part 27 has the role of making the air from said artificial respirator difficult to flow into the air flow path 23 when, for example, the respiratory-side adaptor 21 of the airway adaptor 10 has been connected to the artificial respirator that constantly supplies air.

In this way, because the airway adaptor 10 of this embodiment is provided with the partial shielding part 27 in the proximity of the first aperture 25, this can prevent thinning of the air exhaled by the person being measured and that flows into the air flow path 23 from the second aperture 26 by the constant air flown from said artificial respirator at the center of the air flow path 23, in other words, the part where said pair of translucent windows 24 is provided. Therefore, this allows accurate measurement of the concentration of the component subjected to measurement included in the air exhaled by the person being measured.

In the airway adaptor 10 of this embodiment, the installation location of the partial shielding part 27 is not limited to the proximity of the first aperture 25 on the air flow path 23. For example, the partial shielding part 27 may be provided further to the side of the first aperture 25 instead of the center of the air flow path 23, in other words, the part where said pair of translucent windows 24 is provided. Also, in this case, thinning of the air exhaled by the person being measured by the constant air [flow] mentioned above in the center of the air flow path 23 can be prevented.

Also, in the airway adaptor 10 of this embodiment, said pair of translucent windows 24 may be provided at the inner wall located on the side of the air flow path 23, that is to say, at the location along both sidewalls of the air flow path 23 during the use of said airway adaptor 10. Dew condensation water generated inside the air flow path 23 by the air passing through air flow path 23, or that has flown into the inside of the air flow path 23 from the outside, flows along the bottom wall of the air flow path 23, so its contamination of the translucent windows 24 can be prevented by placing the translucent windows 24 as mentioned above.

In the airway adaptor 10 of this embodiment, not only may the translucent windows 24 be placed as described above, as shown in FIG. 5 to FIG. 8, but the partial shielding part 27 may also be provided so that it does not shield the lower side of the air flow path 23. Therefore, said dew condensation water is not stopped at partial shielding part 27, then will not accumulate inside the air flow path 23, preventing it from contaminating the translucent windows 24.

In the airway adaptor 10 of this embodiment, partial shielding part 27 may be provided integrally with a tube 20. Therefore, the partial shielding part 27 can be provided with the tube 20 without increasing the number of components.

The partial shielding part 27 may be provided as a separate component from the tube 20. By providing the partial shielding part 27 as a separate component, for example, when the person to be measured is an infant, who has a small exhaust breath pressure, the partial shielding part 27 can be installed at the tube 20, as needed, when there is the need to allow the constant air flow to pass easily into the tube 20.

Regarding the airway adaptor 10 of this embodiment, without being limited to the configuration mentioned above, it may be configured so that it is connected to a respiratory concentration measurement device for measuring the concentration of a component acquired from a sample of breath from a person to be measured by, for example, the sidestream method. Specifically, it may be configured so that sampling of exhaled air from a person to be measured is possible by providing a sampling port at the center of the air flow path 23, instead of providing a pair of translucent windows.

In addition, the airway adaptor 10 may be configured to be a differential pressure-type flow rate measurement sensor, by providing pressure outlets for measuring the flow rate of the exhaled air to each respiratory-side adaptor 21 and patient-side adaptor 22 in the airway adaptor 10, and placing a securing part inside the air flow path 23 between each pressure outlet.

Figure 9:
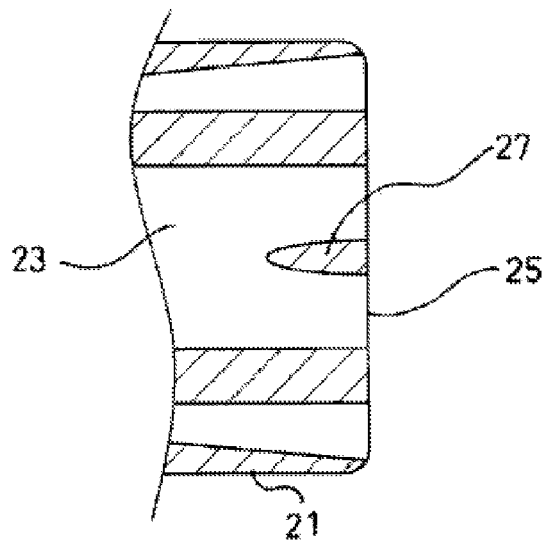
FIG. 9 is an enlarged sectional view showing an enlarged view in the proximity of the first aperture of section C-C of FIG. 6.
Figure 10:
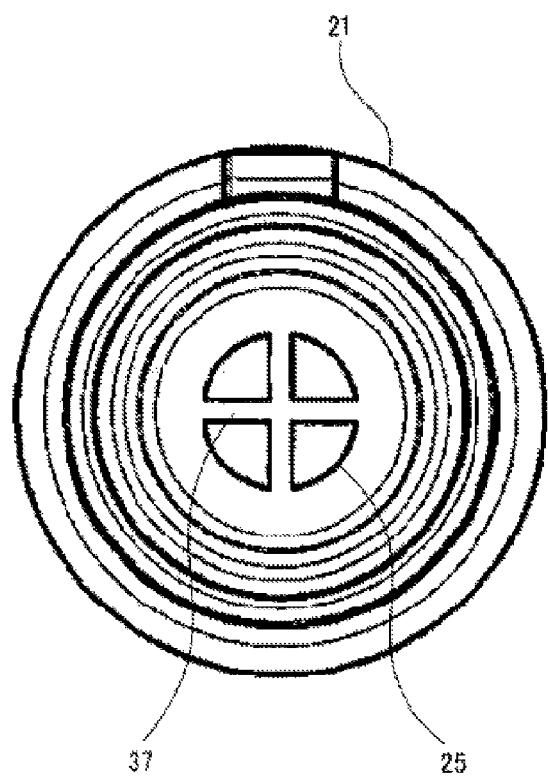
FIG. 10 is a right side view of the airway adaptor equipped with partial shielding materials.
Figure 11:
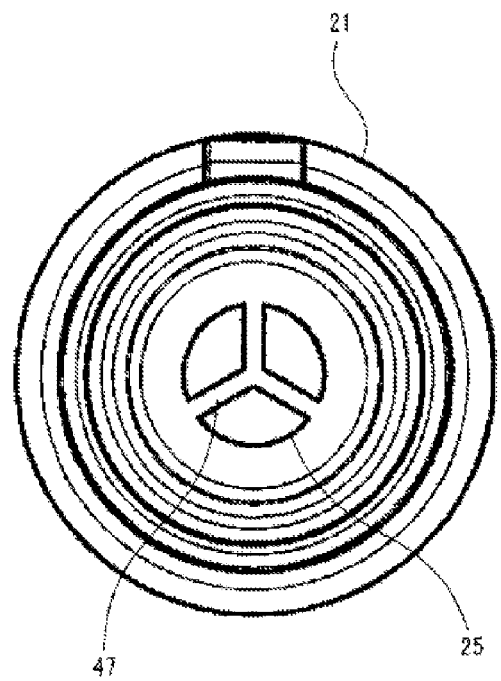
FIG. 11 is a right side view of the airway adaptor equipped with partial shielding materials.
Figure 12:
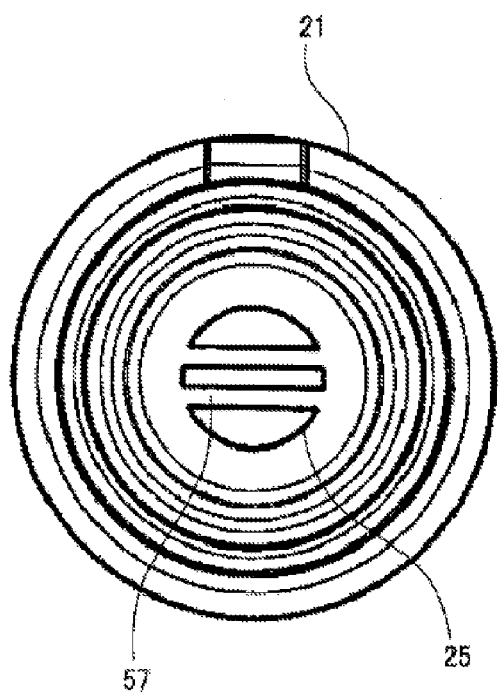
FIG. 12 is a right side view of the airway adaptor equipped with partial shielding materials.
Figure 13:
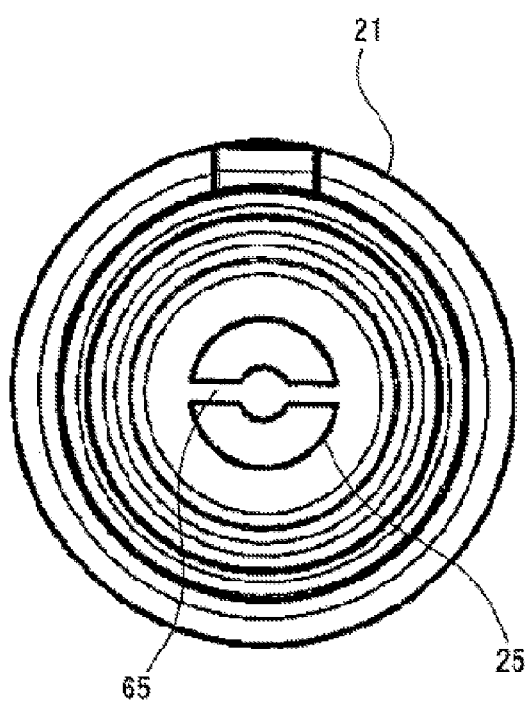
FIG. 13 is a right side view of the airway adaptor equipped with partial shielding materials.

FIG. 9 is an enlarged sectional view showing an enlarged view in the proximity of the first aperture 25 of section C-C of FIG. 6. As shown in FIG. 9, in the airway adaptor 10 of this embodiment, the width of the cross section that cuts, in parallel, the partial shielding part 27 with the inner wall of the air flow path 23, in other words, the length in the vertical direction in the cross section of the partial shielding part 27 as shown in FIG. 9 is narrower toward the second aperture 26 (left side of FIG. 9) than toward the first aperture 25 (right side of FIG. 9).

Forming the sectional structure of the partial shielding part 27 in such a shape can reduce the resistance that forms when the air current generated when exhausting the exhaled air from the person to be measured from airway adaptor 10, in other words, the air current that passes from the left side to the right side in FIG. 9 in the air flow path 23, hits the partial shielding part 27.

The shape of the partial shielding part of the presently disclosed subject matter is not limited to the shape of the partial shielding part 27 provided with the airway adaptor 10 of this embodiment. The airway adaptor 10 may be equipped with, for example, partial shielding parts 37, 47, 57, and 67 having the shapes illustrated in FIG. 10 to FIG. 13, instead of the partial shielding part 27. Moreover, similarly to the partial shielding part 27, these partial shielding parts 37, 47, 57, and 67 are preferably provided closer to the side of the first aperture 25 than to the portion where a pair of translucent windows 24 was provided in the airway adaptor 10.

Note that the processing of information in the presently disclosed subject matter may be performed by a processor that may include a computer-readable medium as known to those of ordinary skill in the art.

While this invention has been particularly shown and described with reference to exemplary embodiments thereof, it will be understood by those skilled in the art that various changes in form and details may be made therein without departing from the spirit and scope of the invention as defined by the appended claims.

What is claimed is:

1. An airway adaptor operable to measure a concentration of at least one of a specific component and a flow rate of a supply gas and a return gas, the airway adapter comprising:
a tube having a flow path in which the supply gas and the return gas passes, the tube including only a single partial shielding, a first end having a first aperture for guiding the supply gas into the flow path, and a second end having a second aperture for guiding the return gas; and
a measurement device operable to measure at least one of the supply gas and the return gas in the air flow path, wherein
the partial shielding is located only at an outermost end of the first end of the adapter, and structured to shield a portion of the air flow path, the partial shielding including two elongate structures that extend across an entire width of the flow path and intersect each other in the flow path.

2. The airway adapter according to claim 1, wherein the first end is configured to connect to a supply of a respiratory gas.

3. The airway adapter according to claim 1, wherein the second end is configured to conduct an inhaled or exhaled breath of a person.

4. The airway adapter according to claim 1, wherein the tube further includes an inner wall defining the flow path, and a pair of translucent windows, the translucent windows facing each other along a respective portion of the inner wall, and allowing detection light irradiated from an outside of the tube from the measurement device.

5. The airway adaptor according to claim 4, wherein the pair of translucent windows is provided along the inner wall located at a side of the flow path, and the partial shielding is structured to shield a portion of the flow path excluding at least one of a lower part and an upper part of the flow path.

6. The airway adaptor according to claim 1, wherein the partial shielding extends across and divides the first aperture into at least two apertures.

7. The airway adaptor according to claim 1, wherein the partial shielding is provided integrally with the tube.

8. The airway adaptor according to claim 1, wherein the measurement device further includes a respiratory concentration sensor structured to optically measure a concentration of the specific component.

9. The airway adaptor according to claim 1, wherein the measurement device further includes a respiratory flow rate sensor structured to measure the flow rate.

10. An airway adaptor operable to measure a concentration of at least one of a specific component and a flow rate of a supply gas and a return gas, the airway adapter comprising:
a tube having a flow path in which the supply gas and the return gas passes, the tube including only a single partial shielding, a first end having a first aperture for guiding the supply gas into the flow path, and a second end having a second aperture for guiding the return gas; and
a measurement device operable to measure at least one of the supply gas and the return gas in the air flow path, wherein
the partial shielding is located only at an outermost end of the first end of the adapter, wherein a width of the partial shielding is narrower toward the second aperture end than toward the first aperture end.

11. A method for measuring a concentration of at least one of a specific component and a flow rate of a gas, the method comprising:
providing an airway adapter including, a tube having an air flow path, a first end having a first aperture, a second end having a second aperture, and a single cross-shaped partial shielding extending across an entire width of the flow path and located only at an outermost end of the first end of the tube;
connecting the first end of the airway adapter to a supply gas;
connecting the second end of the airway adapter to a return gas;
guiding the supply gas into the flow path, and guiding the return gas into the flow path;

measuring at least one of the supply gas and the return gas in the air flow path; and shielding, with the cross-shaped partial shielding, a portion of the air flow path not including a lower most portion of the flow path such that accumulation of dew on the partial shielding is avoided.

12. The method according to claim 11, wherein connecting the first end of the airway adapter includes connecting the airway adapter to a supply of a respiratory gas.

13. The method according to claim 11, wherein connecting the second end of the airway adapter includes connecting the airway adapter to an inhaled or exhaled breath of a person.

14. The method according to claim 11, wherein measuring includes allowing detection light irradiated from an outside of the tube from a measurement device.

15. The method according to claim 14, wherein measuring includes optically measuring a concentration of the specific component of the at least one of the supply gas and the return gas.

16. The method according to claim 11, wherein measuring includes measuring the flow rate of the at least one of the supply gas and the return gas.

17. A system for measuring a concentration of at least one of a specific component and a flow rate of a supply gas and a return gas, the system comprising:

a tube having a flow path in which the gas passes, the tube including a single partial shielding, a first end having a first aperture for guiding the supply gas into the flow path, and a second end having a second aperture for guiding the return gas, the tube including a top portion and a bottom portion;

a measurement device operable to measure at least one of the supply gas and the return gas in the air flow path, wherein the partial shielding is located only at an outermost end of the first end of the tube and extends from the first aperture and terminates in the flow path at a position intermediate the first and second apertures, and structured to shield a portion of the air flow path, the partial shielding also extending from a portion of the tube spaced from a lower most portion of the bottom portion of the tube in the flow path such that accumulation of dew on the partial shielding is prevented;

a processor; and a memory, wherein the processor is structured to determine at least one of a concentration of the specific component and the flow rate.

18. The system according to claim 17, wherein the measurement device includes a respiratory concentration sensor structured to optically measure the concentration of the specific component.

19. The system according to claim 17, wherein the measurement device includes a respiratory flow rate sensor structured to measure the flow rate of the at least one of the supply gas and the return gas.

20. The system according to claim 17, wherein the partial shielding is located closer to the first aperture than the second aperture, and extends across and divides the first aperture into at least two apertures.

* * * * *